(12) United States Patent
Hertens et al.

(10) Patent No.: US 8,184,290 B2
(45) Date of Patent: May 22, 2012

(54) DEVICE AND METHOD FOR MONITORING THE PARTICLE CONTAMINATION IN FLOWING HYDRAULIC FLUIDS

(75) Inventors: Delphine Hertens, Toulouse (FR); Gerhard Mueller, Grafind (DE); Wolfgang Legner, Hoehenkirchen-Siegertsbrunn (DE); Wilhelm Ficker, Poering (DE); Thomas Ziemann, Inning am Holz (DE); Reinhard Reischl, Grosshelfendorf (DE); Marius Bebesel, Munich (DE)

(73) Assignee: Airbus Operations SAS, Toulouse (FR)

( * ) Notice: Subject to any disclaimer, the term of this patent is extended or adjusted under 35 U.S.C. 154(b) by 533 days.

(21) Appl. No.: 12/519,366

(22) PCT Filed: Dec. 18, 2006

(86) PCT No.: PCT/IB2006/004089
§ 371 (c)(1),
(2), (4) Date: Jun. 16, 2009

(87) PCT Pub. No.: WO2008/075128
PCT Pub. Date: Jun. 26, 2008

(65) Prior Publication Data
US 2010/0027006 A1    Feb. 4, 2010

(51) Int. Cl.
*G01N 15/02* (2006.01)
*G01N 21/00* (2006.01)
(52) U.S. Cl. ........................................ 356/335; 356/337
(58) Field of Classification Search .... 356/237.1–241.6, 356/242.1–243.8, 335–344, 426–448, 450–458, 356/600–640
See application file for complete search history.

(56) References Cited

U.S. PATENT DOCUMENTS

| | | | | | |
|---|---|---|---|---|---|
| 4,348,111 | A * | 9/1982 | Goulas et al. | .................. | 356/336 |
| 5,194,910 | A * | 3/1993 | Kirkpatrick et al. | ............ | 356/70 |
| 5,619,333 | A * | 4/1997 | Staff et al. | ...................... | 356/436 |
| 6,331,704 | B1 * | 12/2001 | Owen | ...................... | 250/339.11 |
| 6,532,067 | B1 * | 3/2003 | Chang et al. | .................. | 356/318 |
| 7,382,452 | B2 * | 6/2008 | Groner et al. | .................. | 356/336 |

FOREIGN PATENT DOCUMENTS

| | | |
|---|---|---|
| DE | 41 18 827 | 6/1992 |
| DE | 41 10 231 | 10/1992 |
| EP | 0 889 318 | 1/1999 |
| RU | 2 092 810 C1 | 10/1997 |
| WO | WO 2005/085771 A2 | 9/2005 |

OTHER PUBLICATIONS

Office Action issued Sep. 21, 2010, in Russian Patent Application No. 2009127810/15(038642) (with partial English translation).
Poley, J. et al., Oil Analysis for Monitoring Hydraulic Oil Systems, A Step-Stage Approach, Journal of the Society of Tribologists and Lubrication Engineers, vol. 46, No. 1, pp. 41-47, XP008084701, (1990).

* cited by examiner

*Primary Examiner* — Gregory J Toatley
*Assistant Examiner* — Jarreas C Underwood
(74) *Attorney, Agent, or Firm* — Oblon, Spivak, McClelland, Maier & Neustadt, L.L.P.

(57) ABSTRACT

A device for monitoring particle contamination in flowing hydraulic fluids includes a mechanism for particle counting and particle sizing. Further, a method for monitoring particle contamination in flowing hydraulic fluids: determines fluid flow velocity; counts particles in the hydraulic fluid passing the light barrier for a fixed period of time; and obtains particle size distribution by using a range of different trigger levels. The monitoring device is insertable into an A/C hydraulic system to enable an online-monitoring of degradation of fluid quality during normal flight operations or on the ground. The device and method help lower costs for A/C maintenance and increase A/C availability since necessary service actions can be scheduled strategically.

10 Claims, 2 Drawing Sheets

DEVICE AND METHOD FOR MONITORING THE PARTICLE CONTAMINATION IN FLOWING HYDRAULIC FLUIDS

BACKGROUND OF THE INVENTION

The present invention relates to a device for monitoring the particle contamination in flowing hydraulic fluids according to the preamble of claim 1 and a method for monitoring the particle contamination according to claim 7.

The quality of hydraulic fluids is essential for ensuring the proper operation of safety-critical subsystems in aircrafts such as flaps, slats, landing gears, etc. Contamination of the hydraulic fluid can severely damage mechanical components in the hydraulic system. Therefore, a stringent contamination control is required at all levels of maintenance to ensure flight safety and the highest degree of hydraulic system readiness.

Contamination present in an operating hydraulic system is normally originated at several different sources. Maintenance malpractices introduce large amounts of external contaminates. Wear and chemical reactions are also factors in hydraulic system contamination. The types of contamination are generally classified as organic, metallic solids, non-metallic solids, foreign fluids, air and water.

Organic solids are produced by wear, oxidation or polymerization. Minute particles of O-rings, seals, gaskets and hoses are present due to wear or chemical reactions.

Metallic contaminates are almost always present in hydraulic systems. These particles are the result of wear and scoring of bare metal parts and plating materials such as silver and chromium.

Inorganic or nonmetallic solids include dust, paint particles, dirt and silicates. These particles are often drawn into a hydraulic system from external sources. Disconnected hoses, lines and components are entry points. The wet surface of a hydraulic piston shaft may also draw some contaminates past the wiper seals and into the hydraulic system.

Air contamination, dissolved, entrained or free floating can adversely affect a hydraulic system. Air entrained hydraulic fluid can cause severe mechanical damage from pump cavitations, system pressure loss or slow or erratic flight control movements.

Water is a serious contaminant of hydraulic systems. Dissolved, emulsified or free water may result in the formation of ice or oxidation or corrosion products of metallic surfaces.

Foreign fluids are generally the result of lube oil, engine fuel or incorrect hydraulic fluid having been inadvertently introduced into the hydraulic system during servicing. The effect of foreign fluids other than water depends on the nature of the contaminant. Compatibility of materials of construction, reactions with hydraulic fluid and water, and changes in flammability and viscosity are all affected. The effects of such contamination may be mild or severe depending on the contaminant, amount (quantity) and length of time it has been in the system.

Contamination in oil is specified from particle count. Two basic methods are used: Laser based particle count analysis equipment gives directly information on particle sizes (micron=$\mu$) and figures within specified size ranges. The other method utilize filtering an oil sample through a very fine mesh filter paper. The particles on the surface of the filter paper are then monitored in a microscope and compared to standard contamination pictures to indicate the degree of contamination.

Instead of specifying particle counts contamination is separated into classes defined in two major systems ISO (International Standard Organization) and NAS (National Airspace Standard). Each class defines a range of counts within an exponential scale. Unfortunately, the two systems are not identical and can not be converted in simple mathematics. However, some simple guidelines can be given. First of all let's look at the two systems.

The NAS system divides particles in 5 ranges. Furthermore, the NAS system specifies different counts within each particle range to score a specific class. In practice, oil samples will show up to gain almost the same NAS class rating within the different particle ranges. The system is designed to match the most common found contamination which has really many small particles and fewer big particles. A typical oil analysis can for example have counts divided in the 5 classes. The resulting NAS class according to NAS1638 is defined as the particle count with the highest (worse) score, and only this class is specified.

Currently the quality of hydraulic fluids is generally monitored off-line. During A/C service, fluid samples are tapped from the hydraulic system and their quality is assessed with laboratory equipment off-line. This procedure is time-consuming and costly. Necessary service actions are taken according to fixed schedules rather than on demand.

U.S. Pat. No. 4,323,843 discloses an apparatus for detecting ferrous contamination in a fluid such as engine transmission lubricant. The apparatus has two spaced apart electrodes, a magnetic flux extending between the electrodes, the lines of force of which are substantially rectilinear, the electrodes being connectable to a circuit for signaling when an electrically conductive path is formed from one electrode to the other by metal particles attracted to the flux and formed into an electrode spanning bridge. For preference the sensor is a hollow plug, which in use is screwed into a transmission housing port, and has a flat end wall in contact with the lubricant in the housing. The plug contains a magnet having both poles disposed towards the plug end wall, a portion of the end wall acting as one electrode. A ferromagnetic disc mounted externally from the plug end wall, and electrically insulated therefrom, overlies the poles. The disc acts as a second electrode and serves to direct the magnetic flux rectilinearly across the gap between the electrodes. The electrodes are connectable to circuit means whereby a change in inter-electrode resistance may be detected. A major drawback of this detection device is the fact that only ferrous contamination can be detected. Therefore the effectiveness is very limited with respect to the efforts made and the costs involved.

U.S. Pat. No. 5,754,055 describes a lubricating/hydraulic fluid condition monitor in which a coaxial microwave resonator is placed in a fluid conduit to determine changes in the chemical properties and debris concentration is disclosed. Microwave radiation is applied to the resonator for measuring the resonant frequency and resonator Q. An externally powered electric or magnetic field is used to alternately align and misalign debris in the fluid while the resonator properties are being measured. A logic unit automatically generates tables of resonant frequency and Q versus resonator mode and external field strength. This set of tables constitutes a fingerprint of the fluid condition. By matching the fingerprint against a set of fingerprints taken under known conditions, the condition of the fluid is determined. Changes in the fluid's dielectric constant caused by oxidation or the presence of water, changes in the concentration and size of conducting particles from bearing wear, and changes in viscosity all affect the fingerprint; and thus, can be monitored in real time. In a variation of the invention, a lumped-circuit resonator printed on a microwave circuit board is used as the sensor. In a further variation, a transmission-line resonator printed on a microwave circuit board is used as a sensor. In yet another variation the resonator is a lumped circuit wave guide structure through which the fluid flows. In still another variation, time domain reflectometry is used in a transmission line having one end immersed in the fluid. A major drawback of this solution is the use of microwave frequencies which cause problems for in-flight operation. Especially in the vicinity of fly by wire systems this detection device can not be used during operation of an aircraft.

U.S. Pat. No. 4,013,953 discloses an optical oil monitor that measures particle contamination in oil by passing light through an oil sample and picking up the light that is scattered at 90° by the particle contamination and measures chemical breakdown by the attenuation of the light passing substantially straight through the oil with a second photo sensor. Alternately a sample and a reference are passed between the light responsive sensors for error correction and calibration so that each sensor will have an output signal alternating between a sample signal and a reference signal. The sample and reference are housed within a rotor provided with vanes so that it may be driven as a pump by a motor or be driven by fluid flow as a turbine. When the rotor acts as a turbine, the frequency of the light responsive sensors will be correlated to the fluid flow rate indicated by the turbine turns so that an appropriate frequency responsive gauge is provided in circuit to monitor the fluid flow. The peak signals of a peak detector indicating the particle count are summed up to provide an output corresponding to the amount of contamination. Major drawbacks of this device are the complex mechanical construction including a turbine sample rotor in the lubrication oil flow as the main constructive part. This may lead to mechanical defects and failure of the entire hydraulic system. Further, no indication of the particle size can be provided by the known solution. Finally this known solution is costly and uses relatively large space.

SUMMARY OF THE INVENTION

Therefore, it is an object of the present invention to provide a device for monitoring small solid particles having a size range from 0.1 µm to 100 µm in hydraulic fluids which avoids the drawbacks of the prior art. The monitoring device should be insertable into the A/C hydraulic system to enable an online-monitoring of the degradation of the fluid quality during normal flight operations or on the ground. Further the inventive solution should help lowering the costs for A/C maintenance and increase the A/C availability.

These objects are solved by a device having the features of claim 1 and by a method having the features of claim 7. Advantageous embodiments are described in the dependent claims.

The device for monitoring particle contamination in flowing hydraulic fluids according to the present invention is characterized in that it comprises means for particle counting and particle sizing. The device according to the present invention allows online-monitoring of ferrous and non-ferrous small solid particles having a size range from 0.1 µm to 100 µm in hydraulic fluids and avoids the drawbacks of the prior art. The monitoring device is insertable into the A/C hydraulic system to enable an online-monitoring of the degradation of the fluid quality during normal flight operations or on the ground. Further the inventive solution helps lowering the costs for A/C maintenance and increase the A/C availability since necessary service actions can be scheduled strategically. For evaluation of the measurement information, a data processing unit can be provided. The data processing unit may include analog/digital converters, data storage and a CPU for executing test evaluation software. Such software my include a database storing NAS1638 data for data verification. The device according to the present invention can help to maintain the level of particulate matter contamination in A/C hydraulic systems of aircrafts at an acceptable level and ensures minimum degradation of the mechanical components constituting the hydraulic systems.

A preferred embodiment of the present invention is characterized in that the device comprises an optical sensor and a flow sensor. The optical sensor may be a photoelectric slot sensor having a light beam diameter of 100 µm. To determine the particle size and number, a light barrier technique can be used utilizing the shadowing effect upon particle transit to calculate the particle number and particle size.

A preferred embodiment of the present invention is characterized in that two or more optical sensors having different light beam diameters are provided. The light beam diameters may start from 10 µm or 20 µm and range up to a diameter of 100 µm or 150 µm.

A further preferred embodiment of the present invention is characterized in that, the flow sensor is an ultrasonic transducer. The fluid flow measured in flight operation is produced by the hydraulic pump system of the aircraft and might differ because of the particular flight situation. This goes especially for non steady flight situation where sometime high G-forces apply. Further, to be able to use an ultrasonic transducer, the fluid temperature should also be measured to calculate the speed of sound in this fluid. In case of particle contamination monitoring on the ground, the flow velocity may be adjusted to a known value which makes additional flow rate detection unnecessary.

The method for monitoring particle contamination in flowing hydraulic fluids according to the present invention comprises the following steps:

Determining fluid flow velocity;

Counting of particles in hydraulic fluid passing the light barrier for a fixed period of time;

Obtaining particle size distribution by using a range of different trigger levels.

This method can be advantageously used with a device for monitoring particle contamination in flowing hydraulic fluids comprising means for particle counting and particle sizing. Further a data processing unit should be provided to allow storage and evaluation of the data using a respective evaluation software.

According to a preferred embodiment of the present invention repeated measurements of particle contamination are conducted to allow extrapolating the time at which a critical contamination level is likely to be reached. With such information necessary maintenance actions can be scheduled strategically, i.e. together with other maintenance actions.

According to a preferred embodiment of the present invention signal size and signal duration are attributed to particle size. The signal output voltage, which is triggered by particles passing through the optical sensor, can be visualized and evaluated according to the shape (signal width) and the signal amplitude.

According to another preferred embodiment of the present invention the cumulative size spectrum and the differential size spectrum are used for calculating the particle size. This calculation can be verified by using the statistical data according to NAS1638.

According to still another preferred embodiment of the present invention the range of detectable particle diameters is pre-set to 10 µm to 100 µm. This avoids misinterpretation of noise signals as particle counts.

BRIEF DESCRIPTION OF THE DRAWINGS

Further objects, features and advantages of the present invention will become more clear from the following detailed description of preferred embodiments of the present invention shown in the attached drawing wherein.

DETAILED DESCRIPTION OF THE DRAWINGS

Figure 1:
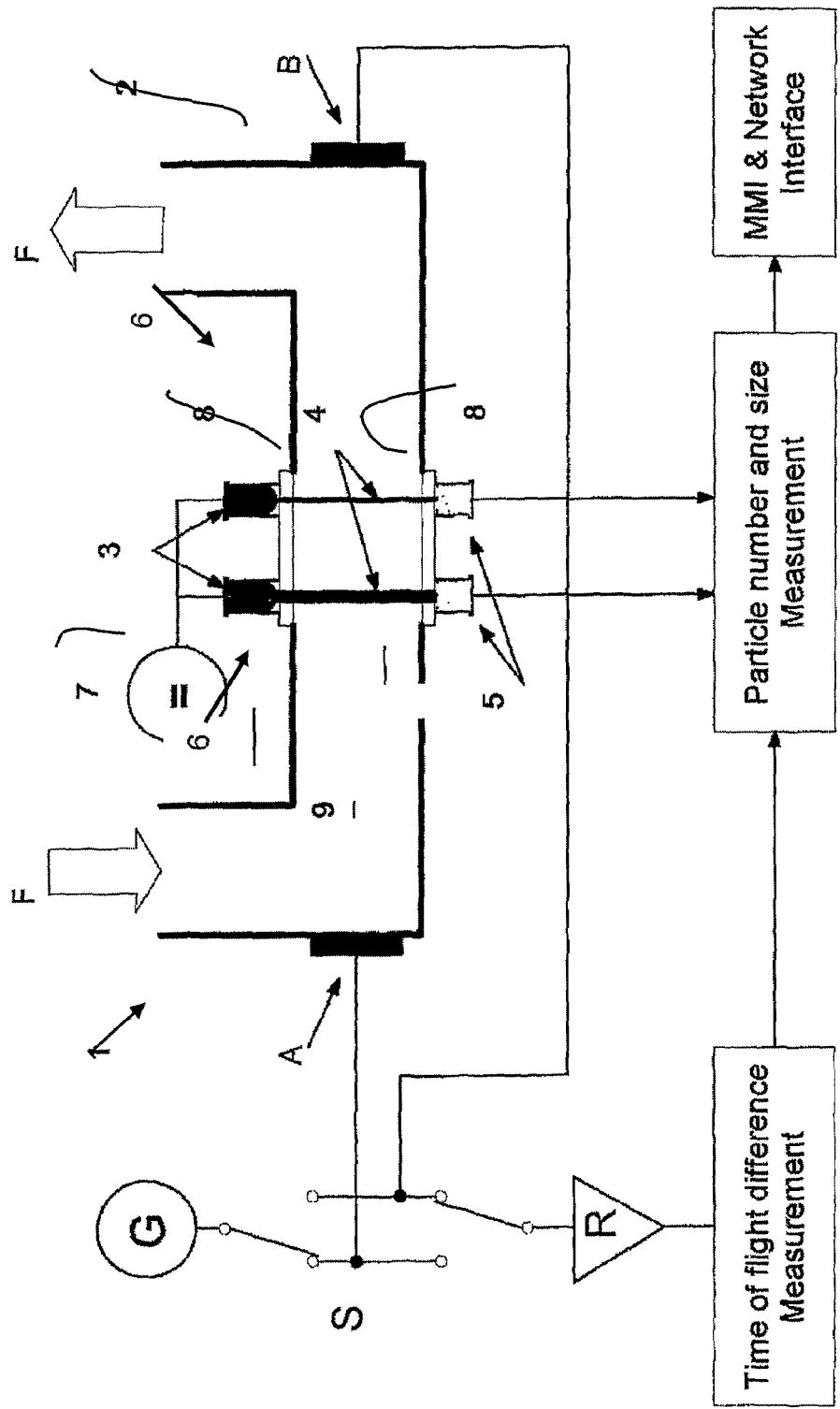
FIG. 1 shows a schematical view of a preferred embodiment of a device according to the present invention.

As shown in FIG. 1, the monitoring device 1 consists of a metal casing 2 containing one or more light barriers 6 for the counting of particles as well as an ultrasonic flow sensor A, B with a built-in temperature sensor (not shown) for enabling a quantitative measurement of the particle size.

The metal casing 2 is constructed as a conduit having in general a circular cross section and bypassing the main hydraulic tubing. The casing 2 therefore has a U-shaped sectional view, as can be taken from FIG. 1. The bypass fluid F enters the casing 2 on the left vertical U-leg and is guided in the horizontal portion of the casing 2 in the center of which the photo sensors of the light barriers 6 are located. Further, on the outer left end of the horizontal U-portion of the casing 2 an ultrasonic transducers A is located and on the outer right end of the horizontal U-portion of the casing 2 an ultrasonic transducers B is located. The flowing hydraulic fluid F is leaving the monitoring device 1 on the right vertical U-leg to re-enter the hydraulic main circuit.

The two light barriers 6 are positioned in a way that the light pass 4 is perpendicular to the direction of the fluid F flow. Optical windows 8 separate optical emitters 3 and optical detectors 5 from the fluid F. The light barriers 6 consist of the optical emitter 3, which in the present prototype is a red-light-LED, and the optical detector 5, which is in this embodiment a silicon photodiode. The sensitive area of the photodiode is determined by the area of an aperture.

The size of the aperture is adjusted to the maximum size of particles to optimize the shadowing effect of a single particle. In the preferred embodiment according to FIG. 1, the left hand light barrier 6 has a larger light beam diameter than the right hand light barrier 6. In the present embodiment the larger light beam diameter is 100 µm and the smaller diameter is 50 µm.

The light barriers 6 are separated from the fluid by means of optical windows 8. In the present embodiment the optical windows are two plane windows positioned on opposite sides of the fluid carrying pipe 9. The windows are sealed by O-rings and fixed by wheel flanges. The LED emitters and photodiode receivers are positioned inside opposite wheel flanges.

The ultrasonic transducers A, B are positioned to emit coaxially with the fluid F flow. The (not shown) temperature sensor is in direct contact with the fluid to allow a measurement of the fluid temperature. The ultrasonic flow sensor consists of two piezo-electric transducers which can either work as a generator G or as a receiver R of ultrasonic sound waves. Both transmitters are positioned coaxially along the direction of the fluid F flow. Both transducers are in direct contact with the fluid and are sealed by means of O-rings and fixed within wheel flanges.

Following, the function of the monitoring device 1 during operation will be described. Particles drifting with the fluid F are detected by means of light barriers 6 which are powered by a constant current 7. LED's are used as light sources and photo diodes are positioned opposite to the LED emitters. The sensitive area of the photodiodes is determined by the size of mechanical apertures. In case a particle passes the light barriers 6, a change in the photo current can be detected. Peak height and width of the photo detector signals depend on the diameter of the shadowing particle as well as on its drift velocity within the fluid F, i.e. on the flow velocity of the fluid F itself.

The size of the particle relative to the size of the apertures on the photo detectors determines the magnitude of the shadowing effect. A large aperture size allows detecting large particles at the expense that small particles produce a shadowing effect that might be too small to detect. A second light barrier 6 with a smaller aperture can increase the shadowing effect of the smaller particles and thus make these detectable. Particles larger than the small-aperture diameter will be misinterpreted as particles with the size of the small-diameter aperture and produce additional wrong counts. As the particle size spectra normally drop off the rapidly with increasing particle size, the number of miscounts by this second light barrier 6 can be tolerated.

In order to enable quantitative particle size measurements, the flow velocity of the fluid is measured by two ultrasonic transducers A, B with the first transducer A emitting in a direction parallel and the second transducer B emitting anti-parallel to the fluid flow. Both transducers A, B are in direct contact with the fluid. The fluid velocity is determined using the time-of-flight measurement principle. This principle uses the difference in the sound propagation times from the emitting to the receiving transducer for sound emitted parallel and anti-parallel to the direction of the fluid flow to determine the flow velocity. The measurement of the time of flight difference is schematically shown on the left hand side and on the bottom of FIG. 1. The function of the ultrasonic transducers A, B as transmitter G or as receiver R is switched by a direction switch S. The measured time difference between the upstream and downstream propagation times is taken as a measure of the fluid flow velocity. The speed of sound in the fluid F depends on the temperature, the fluid temperature needs to be determined for compensation purposes by a separate temperature sensor in direct contact with the fluid F.

Figures 2A, 2B, 2C:
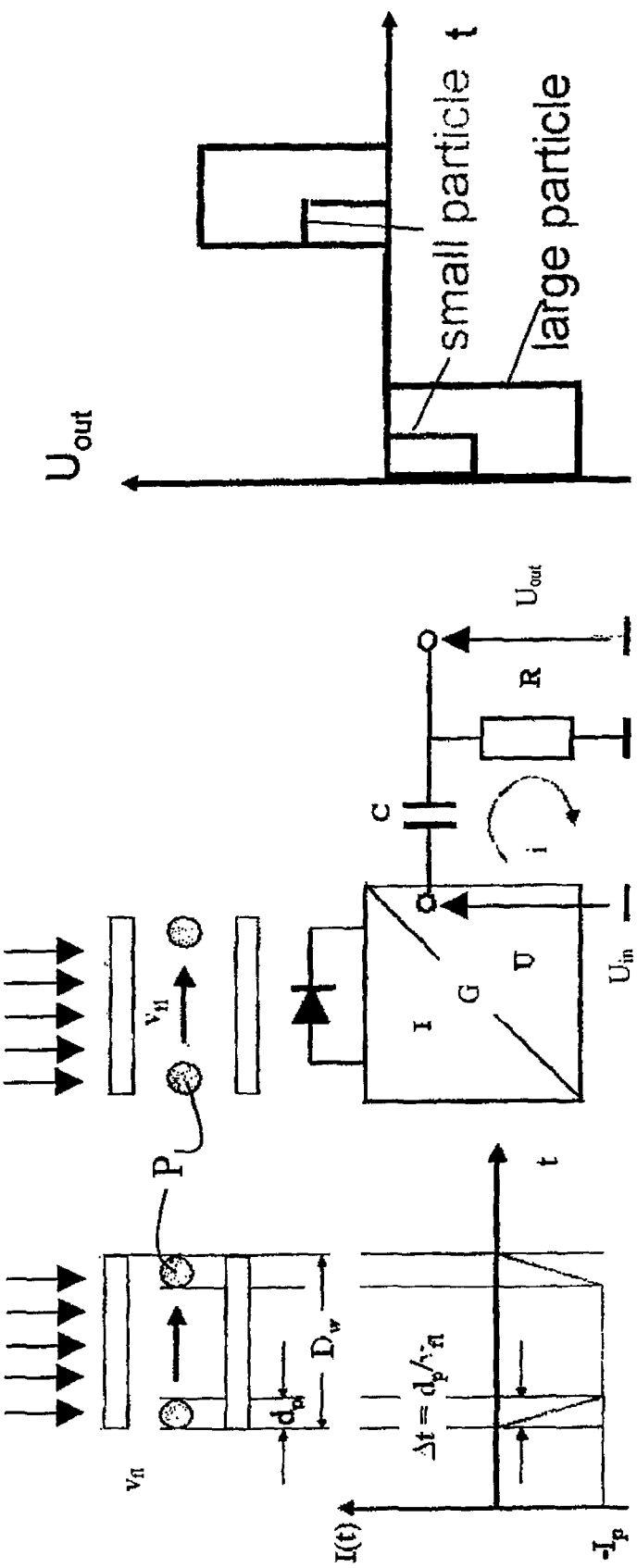
FIG. 2a-c are an explanatory depiction of the functional principle of the device according to the present invention.

FIGS. 2a-2c are an explanatory depiction of the functional principle of the device according to the present invention.

FIG. 2a illustrates the shadowing effect of a single particle P passing a light barrier sensor with a velocity $v_{fl}$ which is the flow velocity of the fluid. In this example the particle size is $d_p$ and the size of the apertures on the photo detector is $D_W$. LED's schematically depicted as arrows are used as light sources and photo diodes are positioned opposite to the LED emitters. The diagram below the sketch in FIG. 2a shows the current over the time, wherein $\Delta t = d_p / v_{fl}$.

FIG. 2b illustrates the generation of the output signal of the optical sensor device by providing a schematic sketch of the electronic circuit.

FIG. 2c shows a schematic output signal of the optical sensor, wherein the output signal of a small particle is shown as a small rectangular function and wherein the output signal of a large size particle is shown as a large rectangular function.

It has to be mentioned that a small light beam/a small window diameter optimizes the shadowing effect and the output signal.

Several embodiments, modifications and variations have been shown and described to illustrate that the basic principles and inventive features of the preferred embodiment are contemplated to be used in further and widely different applications according to the spirit and scope of the invention.

| Reference Numerals | |
|---|---|
| 1 | monitoring device |
| 2 | metal casing |
| 3 | optical emitter |
| 4 | light path |
| 5 | optical detector |
| 6 | light barrier |
| 7 | constant current |
| 8 | optical window |
| 9 | fluid carrying pipe |
| A | ultrasonic transducer |
| B | ultrasonic transducer |
| F | fluid |
| G | transmitter |
| P | particle |
| R | receiver |
| S | direction switch |

The invention claimed is:

1. A device for monitoring particle contamination in flowing hydraulic fluids, comprising:
   means for particle counting and particle sizing; and
   two or more optical sensors having different light beam diameters.

2. A device for monitoring the particle contamination according to claim 1, further comprising an optical sensor and a flow sensor.

3. A device for monitoring the particle contamination according to claim 2, wherein the optical sensor is a photoelectric slot sensor.

4. A device for monitoring the particle contamination according to claim 3, wherein the optical sensor has a light beam diameter of 100 μm.

5. A device for monitoring the particle contamination according to claim 2, wherein the flow sensor is an ultrasonic transducer.

6. A method for monitoring particle contamination in flowing hydraulic fluids, the method comprising:
   determining fluid flow velocity;
   counting particles in hydraulic fluid passing a light barrier for a fixed period of time; and
   obtaining particle size distribution by using a range of different trigger wherein the counting is performed using two or more optical sensors having different light beam diameters.

7. A method according to claim 6, wherein repeated measurements of particle contamination are conducted to allow extrapolating the time at which a critical contamination level is likely to be reached.

8. A method according to claim 6, wherein signal size and signal duration are attributed to particle size.

9. A method according to claim 6, wherein a cumulative size spectrum and a differential size spectrum are used for calculating the particle size.

10. A method according to claim 6, wherein a range of detectable particle diameters is pre-set to 10 μm to 100 μm.

\* \* \* \* \*